(12) United States Patent
Al-Zuhair et al.

(10) Patent No.: US 9,399,740 B2
(45) Date of Patent: Jul. 26, 2016

(54) BIODIESEL PRODUCTION

(75) Inventors: Sulaiman Al-Zuhair, Al-Ain (AE); Ali Al-Marzouqi, Al-Ain (AE); Isameldin Hashim, Al-Ain (AE); Hanifa Eassa Taher, Al-Ain (AE)

(73) Assignee: United Arab Emirates University, Al-Ain (AE)

( * ) Notice: Subject to any disclaimer, the term of this patent is extended or adjusted under 35 U.S.C. 154(b) by 311 days.

(21) Appl. No.: 14/006,542

(22) PCT Filed: Mar. 19, 2012

(86) PCT No.: PCT/GB2012/050596
§ 371 (c)(1),
(2), (4) Date: Nov. 27, 2013

(87) PCT Pub. No.: WO2012/127217
PCT Pub. Date: Sep. 27, 2012

(65) Prior Publication Data
US 2014/0075828 A1 Mar. 20, 2014

(30) Foreign Application Priority Data
Mar. 21, 2011 (GB) .................... 1104761.0

(51) Int. Cl.
*C10G 3/00* (2006.01)
*C12P 7/64* (2006.01)
(52) U.S. Cl.
CPC . *C10G 3/44* (2013.01); *C12P 7/649* (2013.01); *Y02E 50/13* (2013.01); *Y02P 30/20* (2015.11)
(58) Field of Classification Search
CPC .................................................. C12P 7/649
USPC ............................................ 585/240
See application file for complete search history.

(56) References Cited

U.S. PATENT DOCUMENTS

| | | | |
|---|---|---|---|
| 7,772,414 B1 * | 8/2010 | Hybertson | C10L 1/026 554/12 |
| 8,142,830 B2 * | 3/2012 | Marentis | A23L 1/015 426/417 |
| 8,178,326 B2 * | 5/2012 | De Greyt | C12P 7/649 435/134 |
| 8,507,702 B2 * | 8/2013 | Feng | C11C 1/02 554/167 |
| 8,673,028 B2 * | 3/2014 | Savage | C10L 1/026 435/134 |
| 8,747,931 B2 * | 6/2014 | DeLine | A23L 1/1016 426/417 |
| 8,986,400 B2 * | 3/2015 | Feng | C10L 1/191 44/443 |
| 9,109,239 B2 * | 8/2015 | Franklin | A23D 7/00 |

(Continued)

FOREIGN PATENT DOCUMENTS

| | | |
|---|---|---|
| JP | 01-108990 A | 4/1989 |
| JP | 2001-054396 A | 2/2001 |

OTHER PUBLICATIONS

Rathore et al, "Synthesis of biodiesel from edible and non-edible oils in supercritical alcohols and enzymatic synthesis in supercritical carbon dioxide", avialable online at <www.sciencedirect.com>, Apr. 4, 2007, Fuel 86 (2007) 2650-2659.

(Continued)

*Primary Examiner* — Ellen McAvoy
(74) *Attorney, Agent, or Firm* — Katten Muchin Rosenman LLP (57) ABSTRACT

The invention provides a process and reactor system for the production of biodiesel from lamb fats using enzymatic catalysis. Preferably the process comprises two advantageously integrated stages, first of removing fat from the animal meat and second of reacting the removed fat in an enzymatic biodiesel production stage.

21 Claims, 8 Drawing Sheets

(56) References Cited

U.S. PATENT DOCUMENTS

| | | | | |
|---|---|---|---|---|
| 2009/0005582 A1* | 1/2009 | Anderson | ............... | C11C 3/003 554/167 |
| 2010/0209968 A1* | 8/2010 | Akers | .................... | C12N 11/08 435/68.1 |
| 2011/0256282 A1* | 10/2011 | Piechocki | .............. | A21D 2/165 426/321 |
| 2014/0173974 A1* | 6/2014 | Chen | ........................ | C07C 67/08 44/388 |

OTHER PUBLICATIONS

Synder Janel M et al, "Analytical supercritical fluid extraction with lipase catalysis: conversion of different lipids to methyl esters and effect of moisture", Journal of the American Oil Chemists' Society, vol. 74, No. 5, May 1997, pp. 585-588.

Babcock, R. E. et al, "Yield characteristics of biodiesel produced from chicken fat-tall oil blended feedstocks", Department of Transportation, University Transportation Centers Program, Jan. 2008.

Chen C H et al, "Biodiesel production from supercritical carbon dioxide extracted Jatropha oil using subcritical hydrolysis and supercritical methylation", avialable online at <www.sciencedirect.com>, Journal of Supercritcal Fluids, 52, Mar. 1, 2010, 228-234.

Taher H et al, Jun. 15, 2011, "Extracted fat from lamb meat by supercritical CO2 as feedstock for Biodiesel production", Biochemical Engineering Journal 55, pp. 23-31, journal homepage <www.elsevier.com/locate/bej>, available online Apr. 9, 2011.

Anonymous, "Researches create Biodiesel from chicken Fat—Updated", retrieved from <http://www.renewableenergyworld.com/rea/news/article/2008/01/researchers-create-biodiesel-from-chicken-fat-updated-50972>, Jan. 3, 2008.

Al-Zuhair S et al, "Continuous production of biodiesel from fat extracted from lamb meat in supercritical CO2 media", Biochemical Engineering Journal 60 (2012) 106-110, available online Oct. 30, 2011.

International Search Report for International Application No. PCT/GB2012/050596 with a mailing date of Jun. 29, 2012.

* cited by examiner

FIGURE 11

BIODIESEL PRODUCTION

This application is a U.S. national stage application of International Application No. PCT/GB2012/050596, filed Mar. 19, 2012, entitled BIODIESEL PRODUCTION, which claims priority from United Kingdom Application GB 1104761.0, filed Mar. 21, 2011, entitled BIODIESEL PRODUCTION, both of the above-mentioned applications are incorporated herein by reference.

FIELD OF THE INVENTION

The present invention relates a method for production of biodiesel, in particular using fat from lamb meat as a feedstock and involving a lipase-catalysed transesterification reaction carried out in a supercritical carbon dioxide carrier.

BACKGROUND OF THE INVENTION

Biodiesel is a sustainable biofuel derived from vegetable and/or animal fats. Advantageously, it is available from renewable resources and has a less negative environmental impact than fossil fuels.

Traditionally, biodiesel has been produced by transesterification of animal or vegetable fats using a catalyst such as sodium or potassium hydroxide. The transesterification reagent is typically a short chain alcohol such as methanol or ethanol, or a simple aliphatic ester of such an alcohol.

To overcome the drawbacks usually associated with the use of conventional chemical catalyst in biodiesel production, Sake and Kusdiana (*Fuel* 80: 225-231 2001) proposed a non-catalytic process carried out in supercritical methanol. The main advantages of using supercritical alcohols, especially methanol, over conventional catalyzed methods are faster reaction rate, easy product purification and the possibility of using inexpensive, unrefined feedstock (*Ind. Eng. Chem. Res.* 35: 607-612 1996; *Biores. Technol.* 96: 769-777 2005). However, the high critical temperature of methanol renders the process extremely energy intensive.

In another approach, biodiesel can be produced via enzymatic catalysis using a lipase enzyme. This strategy has shown promising results, primarily due to the high selectivity and mild operative conditions of the enzymatic reaction (*J. Biotechnol.* 119: 291-299 2005). In addition, in this process there is no need for feedstock purification, as lipase is capable of transesterifying triglycerides as well as esterifying free fatty acids present in the feedstock (*J. Am. Oil Chem. Soc.*, 73: 1191-1195 1996). The main disadvantage of using lipase is its high cost. Accordingly, it must be used in immobilized form that allows its repeated reuse (*J. Am. Oil Chem. Soc.*, 78: 585-588 2001). Besides reusability, immobilized lipase has been found to have enhanced activity and stability compared to the free form (*Ind. Eng. Chem. Res.*, 43: 1568-1573 2004; *Biores. Technol.*, 100: 5126-5131 2009).

Meanwhile, there remains a demand for inexpensive feedstocks for biodiesel production. This search is driven by the high cost of straight vegetable oils currently used as feedstocks. It has been suggested that use might be made of animal fats that are unsuitable for consumption as food. Such fats, however, generally have high melting points and therefore attempting to liquefy them and then use lipase to catalyse transesterification would lead to denaturation of the lipase. One countermeasure is to dissolve the fat in an organic solvent prior to effecting the enzymatic transesterification reaction (*Biofuels Bioprod. Bioref.*, 1: 57-66 2007; *Biotechnol. Adv.*, 27: 398-408 2009). However, the use of organic solvents has its own disadvantages, such as the introduction of new requirements for solvent separation and recovery.

Supercritical carbon dioxide ($SC-CO_2$) has been used as a carrier for the lipase-catalysed production of biodiesel from vegetable oils (*Fuel* 86: 2650-2659 2007). However, use of $SC-CO_2$ is expensive and therefore this process has not been widely applied. Furthermore, modification of the process to deal with animal fats, which unlike vegetable oils are solids rather than liquids, has not previously been reported.

There is accordingly still a requirement for alternative processes for producing biodiesel, which are procedurally convenient to carry out and which can be carried out on an industrial scale in an economically feasible manner.

One possible source of an animal fat feedstock for biodiesel production would be fat extracted from animal meat. Meat forms a major part of the human diet. Extraction of fat from animal meat prior to its use as a foodstuff is potentially beneficial to health. However, removal of animal fats is not always trivial, particularly when it is present in the meat in the form of intramuscular fat (IMF, commonly known as "marbled fat") rather than as visible fat on the meat surface. For example, meat processors are capable of physically trimming surface fat from meats that have high external fat content, such as beef, so as to produce lean meat. However, marbled fat cannot be removed by such methods. Thus, although low-fat lean meat is readily available from meats such as beef, low-fat meat from sources having high IMF content, for example lamb, is not readily available. Methods to remove lamb fat from lamb meat, such as by solvent or supercritical fluid extraction, are typically prohibitively expensive at present and so are not carried out on an industrial scale. Accordingly, it would also be desirable to render economically feasible a process for generating lean lamb meat.

SUMMARY OF THE INVENTION

The primary object of this invention is to provide a process for producing biodiesel from an animal fat, specifically lamb fat, feedstock. The process must be economically viable on an industrial scale. A further object of the invention is to provide a process that generates lean lamb meat and which uses the extracted lamb fat as a feedstock for biodiesel production. This integrated process is intended to reduce the currently prohibitive cost associated with obtaining lean lamb meat and therefore to open up the possibility of industrial exploitation.

According to the present invention there is provided a process for the production of biodiesel, which process comprises: (A) providing lamb fat in a supercritical carbon dioxide carrier; and (B) reacting said lamb fat in said supercritical carbon dioxide carrier with a $C_{1-5}$ alcohol or $C_{1-5}$ ester thereof in the presence of a lipase catalyst, thereby producing biodiesel.

Preferably, in this process step (A) comprises: (A1) providing lamb meat that has a low concentration of water; and (A2) flowing supercritical carbon dioxide through said meat to extract lamb fat from said meat and thereby provide lamb fat in a supercritical carbon dioxide carrier.

The present invention further provides an integrated reactor system comprising: (I) a fat extraction unit comprising a first reactor for carrying out the step (A2), which unit comprises: (i) means for supplying lamb meat to said first reactor; (ii) means for adjusting the temperature of said first reactor; (iii) means for supplying supercritical carbon dioxide to said first reactor, and (iv) means for removing from said first reactor lamb fat in a supercritical carbon dioxide carrier; and (II) a biodiesel production unit comprising a second reactor for carrying out the step (B), which unit comprises: (v) means for adjusting the temperature of said second reactor; (vi) means for supplying to said second reactor lamb fat in a supercritical carbon dioxide carrier that has been removed from said fat extraction unit; (vii) means for supplying a $C_{1-5}$ alcohol or $C_{1-5}$ ester thereof to said second reactor; and (viii) means for removing biodiesel from said second reactor.

Still further, the present invention provides biodiesel obtainable by carrying out the process of the present invention.

The process of the current invention offers the following advantages:

- There is no need for purification of the feedstock, since the lipase catalyst is capable of catalysing transesterification of both triglycerides and free fatty acids.
- The lamb fat feedstock is of low value and typically would otherwise be a waste product.
- The solid lamb fat feedstock does not need to be dissolved in an organic solvent in order to liquefy it. The inventors have surprisingly found that it is well solubilised by the supercritical carbon dioxide carrier.
- It is not necessary to separate glycerol out of the biodiesel product, since glycerol has low solubility in the supercritical carbon dioxide carrier and so is left in the reactor when the biodiesel product is extracted.

Furthermore, when the process of the step (A) comprises the steps (A1) and (A2), the process of the invention has the following additional advantages:

- The lamb fat extracted from the lamb meat, which is present in the supercritical carbon dioxide carrier, is used directly as a feedstock for production of biodiesel. It is therefore technically routine to operate the process in a continuous manner with supercritical carbon dioxide flowing continuously through the system and whereby lamb meat is supplied and both reduced-fat lamb meat and biodiesel are obtained as commercially valuable final products.
- Moreover, as the energy intensive step of producing supercritical carbon dioxide is required only once, yet generates two commercially valuable products, a significant cost advantage is associated with the process. The process therefore has industrial advantages in comparison with (a) removal of fat from lamb meat by supercritical fluid extraction or (b) generation of biodiesel from lamb fat in isolation.
- Still further, the integrated process is environmentally advantageous as wastage is reduced. In particular, the lamb fat by-product of forming lean lamb meat is not discarded, but instead is processed into environmentally useful biodiesel that can be used as an alternative to fossil fuels.

DETAILED DESCRIPTION OF THE INVENTION

As used herein, the term "lamb meat" means a portion of the edible tissue of a sheep. Typically, this edible tissue is part of the biological tissue of the sheep consisting of skeletal muscle and fat, also commonly known as the "flesh" of the animal. As is well known in the art, lamb meat is often designated according to the specific part of the sheep from it derives. The present invention encompasses all such lamb meat cuts, including scrag end, middle neck, shoulder, best end, loin, breast, chump and leg. By "edible" is meant edible to humans and/or to animal species, typically at least to humans.

For the avoidance of doubt, as used herein "lamb meat" encompasses edible meat obtained from sheep of any age. Thus, "lamb meat" as used herein includes meat that may be sometimes be designated in the art as "lamb", "hogget" or "mutton". Preferably, however, the lamb meat derives from a sheep of under 3 years of age, more preferably under 2 years of age and most preferably of at most one year of age. The lamb meat can also be obtained from any species and breed of sheep, reared in any country in the world.

As used herein, the term "lamb fat" means any fat obtainable from sheep. Preferably in the present invention the lamb fat is obtainable from lamb meat, for example by way of extracting fat from the lamb meat as described herein. Preferably therefore the lamb fat comprises, or consists of, intramuscular fat ("IMF"). However, lamb fat can also be derived directly from the carcass of a sheep, for example by physically cutting away lamb fat from the carcass which is present in the form of surface fat. As would be well known to one of skill in the art, the precise chemical composition of the lamb fat may vary depending on factors such as the breed and age of the sheep from which the fat is derived, the type of fat used, and so on.

As used herein, "biodiesel" means a fuel comprising mono-alkyl esters of long chain fatty acids derived from vegetable oils or animal fats. The biodiesel of the present invention is specifically a product obtainable by carrying out the process of the present invention on lamb fat, i.e. by reacting lamb fat in a supercritical carbon dioxide carrier with a $C_{1-5}$ alcohol or $C_{1-5}$ ester thereof in the presence of a lipase catalyst. Preferably the biodiesel meets the requirements of international standard ASTM D 6751. As is well known in the art, biodiesel can either be used as such (designated as B100—where 100 indicates that the product is 100% biodiesel) or as a blend with a non-biodiesel petroleum-based diesel product (designate as Bxx—where xx indicates the volume percentage of biodiesel fuel in the blend, e.g. B60 represents a blend containing 60% by volume of biodiesel).

The process of the present invention involves providing lamb fat in a supercritical carbon dioxide carrier. This means that the lamb fat is carried by the supercritical carbon dioxide fluid, i.e. it is dissolved in it. This can be achieved by flowing supercritical carbon dioxide through lamb fat. In one embodiment the supercritical carbon dioxide flows through lamb meat that contains lamb fat, thereby extracting lamb fat from the meat and dissolving it in the supercritical carbon dioxide. The present inventors have found that lamb fat is readily soluble in supercritical carbon dioxide.

A supercritical fluid is a state of matter of a substance that is formed when the ambient temperature exceeds the temperature of the vapour-liquid critical point of the substance and the ambient pressure exceeds the pressure of the critical point of the substance (i.e., where the vapour-liquid critical point occurs at a temperature $T_c$ and a pressure $p_c$, a supercritical fluid is present when the temperature T and the pressure p satisfy the inequalities $T>T_c$ and $p>p_c$). The vapour-liquid critical point of a substance is the combination of temperature and pressure where the phase boundary between vapour and liquid ceases to exist.

Properties of supercritical fluids can be changed from gas-like to liquid-like values by adjusting the pressure and temperature. The general properties of supercritical fluids are well known to those of skill in the art and so do not require detailed explanation.

According to the present invention, supercritical carbon dioxide ($SC-CO_2$) is used as a supercritical fluid carrier. $CO_2$ is a non-toxic, non-hazardous, chemically stable, inexpensive, environmentally acceptable solvent and can easily be separated from the products. The supercritical carbon dioxide carrier may consist of pure supercritical carbon dioxide or it may be a mixture of supercritical carbon dioxide and one or more other compounds, for example a mixture of $CO_2$ and ethane or $CO_2$ and propane. Most preferably, though, the supercritical fluid is substantially pure supercritical carbon dioxide, i.e. supercritical carbon dioxide of 95-100% purity or 98-100% purity or even 99-100% purity, such as substantially 100% purity.

In the present invention, the lamb fat, which is in (i.e., dissolved in) the supercritical carbon dioxide carrier is reacted with a $C_{1-5}$ alcohol or $C_{1-5}$ ester thereof in the presence of a lipase catalyst, thereby producing biodiesel. The primary chemical reactions occurring in this process involve transesterification. Specifically triglycerides in the lamb fat react with the $C_{1-5}$ alcohol or $C_{1-5}$ ester thereof so as to produce esters of the $C_{1-5}$ alcohol or $C_{1-5}$ ester thereof (the desired monoalkyl esters) as well as glycerol as a by-product.

Preferably the $C_{1-5}$ alcohol or $C_{1-5}$ ester thereof is selected from the group consisting of methanol, ethanol, methyl methanoate, methyl ethanoate, ethyl methanoate and ethyl ethanoate. More preferably, the $C_{1-5}$ alcohol or $C_{1-5}$ ester thereof is ethanol or methanol, and most preferably it is methanol.

Preferably the molar ratio of $C_{1-5}$ alcohol or $C_{1-5}$ ester thereof to triglycerides in said lamb fat is from 2:1 to 6:1, more preferably from 3:1 to 5:1 and most preferably from 3.5:1 to 4.5:1.

Optionally the $C_{1-5}$ alcohol or $C_{1-5}$ ester thereof used in the process of the present invention can be provided in the form of a mixture with one or more other $C_{1-5}$ alcohols or $C_{1-5}$ esters thereof and/or with one or more carrier chemicals. In one preferred embodiment a mixture of butanol (e.g., t-butanol) and another $C_{1-5}$ alcohol or $C_{1-5}$ ester thereof is used (e.g., ethanol and/or methanol, preferably methanol). The advantage of using butanol (e.g., t-butanol) in the process is that it has a favourable effect on lipase activity stabilization. As the skilled person would appreciate, it may be advantageous to use mixtures (e.g., with an inert carrier) in order to adjust the overall flow rate in the process of the $C_{1-5}$ alcohol or $C_{1-5}$ ester thereof that is taking part in the reaction.

The lipase enzyme may be any lipase enzyme that is capable of catalysing the transesterification reaction between triglycerides in the lamb fat and the of $C_{1-5}$ alcohol or $C_{1-5}$ ester thereof. A person skilled in the art would be familiar with the use of lipase enzymes in biodiesel production and so would have no difficulty in selecting an appropriate enzyme for use in the process of the present invention. It is also a matter of routine laboratory practice to confirm that a particular chosen lipase enzyme has catalytic activity for the transesterification reaction between triglycerides in the lamb fat and the of $C_{1-5}$ alcohol or $C_{1-5}$ ester thereof, e.g., by carrying out the protocol described in the Examples section of this application and then determining whether or not mono-alkyl esters of long chain fatty acids are produced as desired.

Preferably the lipase enzyme is used in an immobilized form, typically by immobilization on an inert substrate. The use of immobilized lipase enzyme is known in the biodiesel production industry and immobilized lipase enzyme is commercially available. The primary advantage of using immobilized lipase enzyme is that it can be used repeatedly. However, besides reusability, immobilized lipase has enhanced activity and stability compared to the free form.

One suitable class of lipase enzymes for use in the process of the present invention are lipase enzymes derivable from the *Candida Antarctica* yeast species. One exemplary lipase enzyme for use in the process of the present invention is the Novozyme 435 enzyme, which is a lipase acrylic resin (i.e., an immobilized lipase) that is derived from *Candida Antarctica* and which is commercially available from Sigma-Aldrich.

Preferably the amount of enzyme used, as a weight ratio to the amount of lamb fat feedstock, is from 10% to 50%, more preferably from 10% to 40%, and most preferably from 10% to 30%, for example 20% to 30%.

The catalytic reaction between the lamb fat and the $C_{1-5}$ alcohol or $C_{1-5}$ ester thereof is preferably carried out at a reaction temperature of from 20 to 50° C., more preferably from 35 to 50° C. and most preferably from 40 to 50° C., for example from about 45 to 50° C. Typically higher temperatures within these ranges increase the reaction rate constants and so favour high biodiesel yields. However, it is important to avoid denaturing the lipase enzyme, which occurs to a significant degree at temperatures in excess of 50° C.

The catalytic reaction occurs under a suitable pressure to ensure that the carbon dioxide carrier is in supercritical fluid form and that the lamb fat is contained within the carrier. Preferably the pressure is greater than or equal to, and preferably greater than, $1 \times 10^7$ Pa. In further preferred embodiments, the pressure is: greater than or equal to, and preferably greater than, $3 \times 10^7$ Pa; at least $4 \times 10^7$ Pa; or about $5 \times 10^7$ Pa. However, the pressure is preferably not more than $5 \times 10^8$ Pa, for example not more than $1 \times 10^8$ Pa. One particularly preferred range is $4 \times 10^7$ Pa to $5 \times 10^8$ Pa. Another particularly preferred range is $1 \times 10^7$ Pa to $3 \times 10^7$ Pa.

For the avoidance of doubt, it should be noted that it is the inevitable result of the reaction between the lamb fat and the $C_{1-5}$ alcohol or $C_{1-5}$ ester thereof that biodiesel is produced. Therefore any reference to "thereby producing biodiesel" in relation to this reaction step is present for ease of understanding.

The process of the present invention preferably comprises a step of providing lamb meat that has a low concentration of water. Typically, this means that the concentration of water in the meat is less than 30% by weight (hereinafter designated as wt %). Preferably the concentration of water in the meat is 20 wt % or less, more preferably 15% wt % or less and most preferably 10 wt % or less. For example, the concentration of water in the meat may be as low as 5 wt % or less.

In one embodiment, the step of providing lamb meat that has a low concentration of water consists of providing a commercially available lamb meat that has a low concentration of water. For example, the lamb meat may be a lamb jerky (jerky is a commercially available source of dried meat). Where the lamb meat already has a sufficiently low water concentration, it is not necessary to carry out further dehydration before the step of flowing a supercritical fluid through the meat.

In another embodiment, the step of providing lamb meat that has a low concentration of water comprises: (i) providing lamb meat; and (ii) reducing the concentration of water in the meat. In this embodiment, the lamb meat may be a commercially available source of cooked, partially cooked, or raw lamb. Preferably, though, the lamb meat is raw. The lamb meat may have been subjected to prior dehydration (for example, it may be a lamb jerky), or alternatively it may be simply an "untreated" lamb meat that has not been subjected to any dehydration procedures. Most typically, the lamb meat used in this embodiment of the process of the present invention has not been pre-treated, for example by already having been subjected to the process of the present invention. Such "untreated" lamb meat generally contains water in an amount of the order of 65 wt %, for example in an amount of from 50-80 wt %, preferably 55-75 wt % or most preferably 60-70 wt %. It will of course be appreciated that in this embodiment which comprises a specific step of reducing the concentration of water in the meat there is no restriction on the quantity of water present in the initial meat.

Reducing the concentration of water in the meat can be carried out using any suitable means for removing water from meat sources. Methods for removing water from meat are well known in the art. Freeze-drying (sometimes known as lyophilization) is one suitable method. Vacuum-drying is another suitable method. Both of these techniques are common in the food industry and can therefore be carried out as a matter of routine on an industrial scale. Accordingly, in a preferred embodiment the step of reducing the concentration of water in the meat comprises, or consists of, freeze-drying or vacuum-drying the meat.

Vacuum-drying involves drying the meat under reduced pressure and usually under heating (for example, to about 40-100° C., preferably to about 50-90° C. and more preferably to about 60-80° C., such as to about 70° C.) to reduce its moisture content. The present inventors have found when vacuum-drying is used to reduce the concentration of water in the meat as part of the process of the present invention, particularly high levels of fat can be extracted from the meat. Accordingly, in a particularly preferred embodiment of the invention the step of reducing the concentration of water in the meat comprises, or consists of, vacuum-drying the meat. However, as vacuum drying is carried out at elevated temperature in another preferred embodiment the step of reducing the concentration of water in the meat does not comprise vacuum-drying the meat.

The present inventors have also found that freeze-drying gives good results. As freeze-drying is typically carried out at lower temperatures than vacuum drying, it has less of an effect on the overall quality of the meat. Accordingly, in a further particularly preferred embodiment of the invention the step of reducing the concentration of water in the meat comprises, or consists of, freeze-drying the meat.

Spray-drying and air drying can also be used to dry the meat. However, both freeze-drying and vacuum-drying give better results than either spray-drying or air drying. Preferably, therefore, the process of the invention does not comprise spray-drying or air drying the meat.

When the process comprises a step (A1) of providing lamb meat that has a low concentration of water, it is necessary also to carry out a step (A2) of flowing supercritical carbon dioxide through this meat, in order to extract lamb fat from said meat and thereby provide lamb fat in a supercritical carbon dioxide carrier. In this embodiment of the invention it is this lamb fat in a supercritical carbon dioxide carrier that then undergoes the catalytic transesterification reaction in step (B).

Step (A2) is thus a step of extracting lamb fat from lamb meat by supercritical fluid extraction. Experimental apparatuses for carrying out such a supercritical fluid extraction are commercially available. Typically, the meat is loaded into a chamber and then the supercritical carbon dioxide is flowed through the meat at an appropriate temperature, pressure and flow rate. Fat is extracted from the meat by the flowing supercritical carbon dioxide and removed from the chamber together with the exiting supercritical carbon dioxide.

It is not essential that the meat is ground up before the step (A2). However, in a preferred embodiment of the invention, the meat is ground up before step (A2). Grinding increases the surface area of the meat and has been found to improve the amount of fat removed. In an embodiment which involves reducing the concentration of water in the meat, the grinding can of course be carried out either before or after the step of reducing the concentration of water in the meat. In a particularly preferred embodiment, the meat is ground after a step of reducing the concentration of water in the meat but before the step of flowing the supercritical fluid through the meat.

In a preferred embodiment of the present invention, at least 55% of the fat originally present in the meat is extracted therefrom. This means that at the end of the process of the present invention at least 55% of the fat has been removed from the meat when compared with the amount of fat present before the process of the present invention was started. More preferably, at least 60% of the fat originally present in the meat is extracted therefrom, for example at least 70%. Typically, up to 90% of the fat originally present in the meat is extracted therefrom. Clearly the maximum amount of fat that can be extracted is 100%.

The present inventors have also found that certain specific supercritical fluid extraction conditions lead to a particularly advantageous degree of fat extraction in the step (A2).

In particular, in step (A2) it is preferable that the supercritical carbon dioxide flows through the meat at a flow rate per gram of meat of less than or equal to, and preferably less than, 3.3 ml $min^{-1}$ per gram. More preferably, the supercritical carbon dioxide flows through the meat at a flow rate per gram of not greater than 2.7 ml $min^{-1}$ per gram. Most preferably, the supercritical carbon dioxide flows through the meat at a flow rate per gram of about 2 ml $min^{-1}$ per gram. However, flow rates per gram are preferably at least 0.3 ml $min^{-1}$ per gram, for example at least 0.7 ml $min^{-1}$ per gram. One particularly preferred range is 0.3 ml $min^{-1}$ to 2.7 ml $min^{-1}$ per gram.

Furthermore, in step (A2) preferably the supercritical carbon dioxide flows through the meat at a pressure of greater than or equal to, and preferably greater than, $1 \times 10^7$ Pa. It is more preferable that the supercritical carbon dioxide flows through the meat at a pressure of greater than or equal to, and preferably greater than, $3 \times 10^7$ Pa. More preferably still, the supercritical carbon dioxide flows through the meat at a pressure of at least $4 \times 10^7$ Pa. Most preferably, the supercritical carbon dioxide flows through the meat at a pressure of about $5 \times 10^7$ Pa. However, the pressure is preferably not more than $5 \times 10^8$ Pa, for example not more than $1 \times 10^8$ Pa. One particularly preferred range is $4 \times 10^7$ Pa to $5 \times 10^8$ Pa.

Still further, in step (A2) it is preferable that the supercritical carbon dioxide flows through the meat at a temperature of greater than or equal to, and preferably greater than, 35° C., for example a temperature of at least 55° C. Preferably the temperature is not more than 100° C., for example not more than 80° C. One particularly preferred range is 35° C. to 80° C.

In a particularly preferred embodiment, in step (A2) the supercritical carbon dioxide flows through the meat at a flow rate per gram of 0.3 ml $min^{-1}$ to 2.7 ml $min^{-1}$ per gram, a pressure of $4 \times 10^7$ Pa to $5 \times 10^8$ Pa and a temperature of 35° C. to 80° C. In a currently most preferred embodiment, the supercritical carbon dioxide flows through the meat at a flow rate per gram of about 2 ml $min^{-1}$ per gram, a pressure of about $5 \times 10^7$ Pa and a temperature of about 55° C.

Typically no fat is added to the meat during the process of the present invention.

In a preferred embodiment of the present invention, the meat obtained after step (A2) is formulated into a food product. By "formulating the lamb meat into a food product" is meant carrying out one or more process steps in order to convert the product produced by step (A2) into a form suitable for consumption by human and/or animal species. For the avoidance of doubt, the term "suitable for consumption" embraces both cooked meat that is directly edible and raw meat that requires cooking to render it edible.

Preferably the step of formulating the lamb meat into a food product comprises hydrating (i.e., adding water to) the product produced after step (A2). For example, a sufficient amount of water may be added so that the water content by weight of the final product is substantially the same as lamb meat that has not been subjected to the process of the present invention. Other routine process steps such as adding preservatives and/or other conventional food additives can also be carried out in this step.

Hydrating a product produced after step (A2) can be carried out by addition of cold or heated water. When the water is heated, for example substantially to boiling point, the time taken for hydration to occur is reduced. Typical times for effecting hydration may be about 2 to 5 minutes when hot, for example boiling, water is used or about 10 to 15 minutes when cold water is used. Roughly two parts of water to one part of meat is suitable for effecting the hydration.

In a further embodiment, the step of formulating the lamb meat into a food product comprises incorporating the product of step (A2) into a dried food product, for example a dried soup or a dried meal, wherein the dried food product is intended for hydration at the point of use.

In a preferred embodiment of the present invention, the step (B) is carried out in a biodiesel production unit comprising a reactor for carrying out the step (B), which unit comprises: means for adjusting the temperature of the reactor; means for supplying to the reactor lamb fat in a supercritical carbon dioxide carrier; means for supplying a $C_{1-5}$ alcohol or $C_{1-5}$ ester thereof to the reactor; and means for removing biodiesel from the reactor. A worker of ordinary skill in the art would be able to provide a suitable reactor as a matter of routine. For the avoidance of doubt, it should be noted that though several of the above-described means are recited as discrete elements, where appropriate several of the means can be provided in the form of a single physical element. For example, if desired a single means (e.g., an inlet tube) can be used to supply to the reactor both the lamb fat in a supercritical carbon dioxide carrier and the $C_{1-5}$ alcohol or $C_{1-5}$ ester thereof.

It will be appreciated that, during operation of the biodiesel production unit, lipase enzyme is present in the reactor (typically in immobilised form). Preferably therefore the reactor comprised in the biodiesel production unit further comprises lipase enzyme, which is preferably immobilised. The lipase enzyme can be packed into the reactor prior to operation by any suitable means, for example by opening up the reactor and placing the enzyme into it, or by supplying it via one or more of the means (e.g., inlet/outlet) tubes for supplying/removing the lamb fat, alcohol or ester thereof or biodiesel. Clearly during operation of the reactor the lipase enzyme must be located so as to contact both the lamb fat in a supercritical carbon dioxide carrier and the $C_{1-5}$ alcohol or $C_{1-5}$ ester thereof.

When the process of the present invention comprises the steps (A1) and (A2), then the step (A2) is preferably carried out in a fat extraction unit comprising a first for carrying out the step (A2), which unit comprises: means for supplying lamb meat to the reactor; means for adjusting the temperature of the reactor; means for supplying supercritical carbon dioxide to the reactor; and means for removing from the reactor lamb fat in a supercritical carbon dioxide carrier. Clearly this reactor must be arranged such that during operation the supercritical carbon dioxide flows through the lamb meat to the means for removing from the reactor lamb fat in a supercritical carbon dioxide carrier. Again, a worker of ordinary skill in the art would be able to provide a suitable reactor as a matter of routine.

Preferably the fat extraction unit further comprises means for generating supercritical carbon dioxide, for example by pressurising a $CO_2$ sample.

In a preferred embodiment of the invention, when the process comprises the steps (A1), (A2) and (B), then it is carried out in an integrated reactor system. This system comprises the above-described fat extraction unit (as a "first" reactor) and the above-described biodiesel production unit (as a "second" reactor). These units are arranged in series, so that during operation lamb fat in a supercritical carbon dioxide carrier emerging from the fat extraction unit is directed into the biodiesel production unit. Thus, the use of the integrated reactor system is advantageous because it is only necessary to carry out once the expensive step of generating supercritical carbon dioxide. The supercritical carbon dioxide is maintained in supercritical fluid form throughout the integrated process. Accordingly, by combining the fat extraction procedure and the biodiesel production procedure in this manner, it now becomes economically feasible to use supercritical fluid techniques both to obtain a desirable lean lamb meat product and to obtain biodiesel derived from lamb fat.

Preferably when the process of the present invention is carried out in the integrated reactor system, the integrated reactor system is adapted so that the first reactor (in the fat extraction unit) and the second reactor (in the biodiesel production unit) operate at substantially the same temperature and pressure. By substantially the same temperature is meant that the temperature in the first reactor and the second reactor differ by not more than 20° C., preferably not more then 10° C., more preferably not more than 5° C. By substantially the same pressure is meant that the pressure in the first reactor and the second reactor differ by not more than $5 \times 10^7$ Pa, preferably not more then $1 \times 10^7$ Pa, more preferably not more than $5 \times 10^6$ Pa. Preferred temperatures for each of the first and second reactors in this embodiment are from 35° C. to 50° C. Preferred pressures for each of the first and second reactors in this embodiment are from $1 \times 10^7$ Pa to $3 \times 10^7$ Pa. Preferably each of the first second reactors operates at a temperature of from 35° C. to 50° C. and a pressure of from $1 \times 10^7$ Pa to $3 \times 10^7$ Pa.

Figure 10:
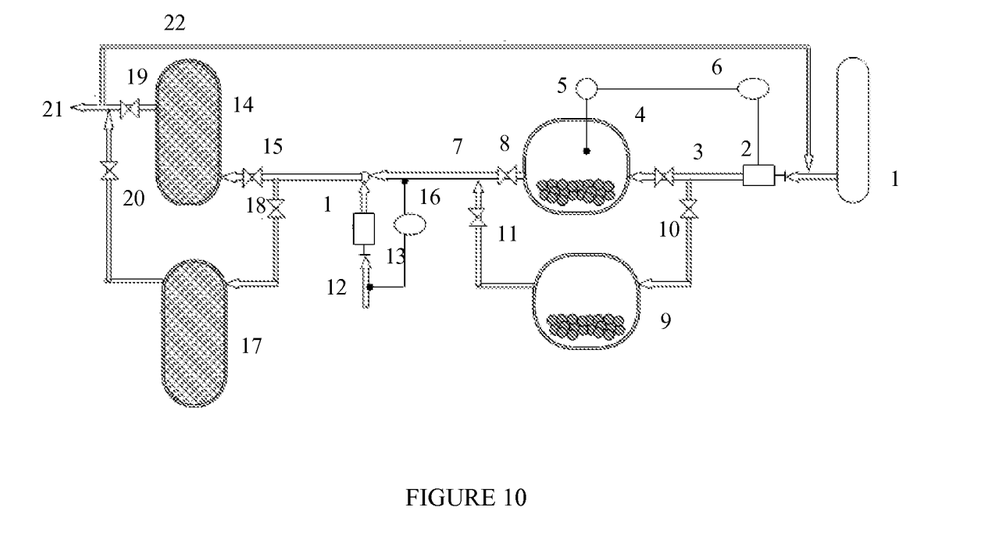
FIG. 10 is a schematic diagram of an exemplary integrated fat extraction-biodiesel production system for carrying out the process of the present invention.

The present invention also extends to the integrated reactor system itself. This system is adapted for carrying out the advantageous process of the present invention. One exemplary system is shown in FIG. 10. A $CO_2$ source [1] is connected to a high pressure pump [2] for pressurising $CO_2$ from the $CO_2$ source [1]. Pressurized $CO_2$ enters via a first valve [3] a first reactor [4] (for fat extraction). The first reactor [4] contains a pressure sensor [5], preferably connected to a pressure controller [6] for adjusting the pressure generated by the pump [2] as required. Supercritical $CO_2$ flows through lamb meat in the first reactor [4] and then emerges via an outlet [7], controlled via a second valve [8]. Optionally, a standby additional first reactor [9] is also provided, with $CO_2$ supply to that standby reactor [9] being controlled via a third valve [10] and exit of $CO_2$ from the standby reactor being controlled via a fourth valve [11]. $C_{1-5}$ alcohol or $C_{1-5}$ ester thereof supplied via a pipe [12] enters a high pressure pump [13] and pressurized alcohol or ester thereof is supplied to a second reactor [14] (for biodiesel production) together with $CO_2$ that has emerged from the first reactor [4] (and the standby first reactor [9] if applicable). Supply of feedstock to the second reator [14] can again be controlled via one or more valves [15]. Typically a flow rate controller [16] can be used to control the relative flow rates of the $CO_2$ and alcohol or ester thereof to desired levels. Again, a standby additional second reactor [17] can optionally be present if desired, with feedstock supply again controlled via one or more valves [18]. The second reactors [14] and [17] contain the lipase catalyst, typically in immobilized form. A further valve [19] is provided for the second reactor [14] (along with a valve [20] for the standby second reactor [17], if applicable). Biodiesel product in $CO_2$ carrier emerges from these valves [19] and [20]. The biodiesel [21] can then separated from the $CO_2$ (e.g., by depressurization) and $CO_2$ recycled via a recycling pipe [22].

The present invention still further provides biodiesel obtainable by carrying out the process of the present invention. The chemical composition of biodiesel is of course dependent on the chemical composition of the feedstock material (e.g., triglyceride content, impurities content, and so on). Therefore the biodiesel product obtained according to the process of the present invention from a lamb fat feedstock will differ from biodiesels obtained from other sources.

The following Examples illustrate the invention.

General Experimental Procedure

The experimental apparatus consisted of a $CO_2$ high pressure syringe pump with a maximum operating pressure of 500 bar, pump controller (Model 260D, ISCO, USA) and SCF extraction unit (ISCO, SFX 220). The supercritical fluid extraction ("SFE") unit consisted of an extraction chamber with two 10 ml stainless steel cells and a temperature controller with a maximum of 150° C. (ISCO, SFX 200). The control panel displayed extraction time, pressure, $CO_2$ flow rate as well as volume of $CO_2$ passed. Pressure within chamber was measured and controlled by the system, while the temperature was measured and controlled by the incubator. The precision of the temperature measurements of extraction system was 0.1° C. To achieve good control of flow rate, a micrometer valve was used.

Approximately 1.5 g of pre-prepared lamb meat sample was loaded into a 10 ml extraction cell with 1.6 cm (⅝ inch) diameter filters in the top and bottom of the cell. The extraction cell was placed in the extraction chamber, where it was allowed to equilibrate to the desired temperature for 15 minutes. $CO_2$ was then flowed from the $CO_2$ cylinder into the high pressure syringe pump. This high pressure pump pressurized the $CO_2$ to the desired pressure. When the desired pressure was reached, the extraction was started by opening a valve between the pump and extraction cell. This allowed $SC-CO_2$ to flow through the extraction cell from the bottom to the top. The sample was held for 15-30 minutes at the desired pressure and temperature to attain equilibrium. Then the exit valve was opened and the fat was separated from extract-$SC-CO_2$ solution and collected in a collection vial.

The extracted fat was weighed using an analytical balance with precision of 0.0001 g (Precisa, XB220A) after each 20 ml of $CO_2$ passed. The extraction yield was determined based on the cumulative mass of the extracted fat divided by the weight of initial prepared sample. Meanwhile, extraction efficiency was determined based on mass of the extracted fat divided by total fat content of meat sample, which was determined using Soxhlet extraction (i.e., carried out using a Soxhlet extractor).

The biodiesel production system was similar to the one used for fat extraction. Compositions of the reaction mixtures consisted of extracted 0.5 g fat and pre-specified amounts of lipase (Novozym 435) and methanol. $SC-CO_2$ flowed from the $CO_2$ cylinder into the high pressure syringe pump and pressurized to the desired pressure of 200 bars. When both the desired pressure and temperature were reached, the reaction was started by allowing the $SC-CO_2$ to fill the reaction cell while keeping the elusion valve sealed. As soon as the desired reaction time was reached, reaction cell was depressurized by opening elution valve. The products were then dissolved in known amount of n-hexane and the fatty acids methyl esters (FAME) content was analyzed using GC. The variation of temperature in the system was controlled with $\pm 1°$ C. and the variation of pressure was $\pm 1$ bar. Effects of reaction temperature, different alcohol to fat molar ratios and enzyme loading on product yield were investigated.

The integrated system consisted of the same above-mentioned two systems connected together. The outflow from the extraction cell was mixed with methanol in the desired ratio and fed continuously, using the same pump to the packed bed bioreactor. The output of the reactor consisted mainly of the biodiesel. A low flow rate of 0.5 ml min$^{-1}$ was chosen to be passed through the extraction-reaction integrated cell in order to increase the residence time. The reaction cell, of 10 ml total volume, was completely packed with immobilized lipase. The chosen operating conditions in the fat extraction stage were 45° C. and 200 bars, at which the solubility of fat in $SC-CO_2$ was found, from the batch extraction experiment, to be 0.0025 g m$^{-1}$. The reaction temperature in the biodiesel production stage was chosen to be 50° C.

The minimum volume percentage of methanol stream that could be added to the main $SC-CO_2$ stream was 1%. However, the volume flow rate of methanol required to make the molar ratio of methanol:fat ratio equal 4:1, the optimum as found in the batch reaction experiment, was 0.05%. Therefore, methanol was diluted 20 times in t-butanol, and the solution with flow rate that accounted for 1% of the total volume was passed, in order to provide methanol in the desired molar ratio. t-Butanol was chosen because of its favourable effect on lipase activity stabilization (*J. Biosci. Bioeng.*, 95: 466-469 2003).

About 2.5 g freeze-dried samples were charged into the extraction cell, and were replaced three times using the same enzyme in the reaction cell. The packed bed bioreactor was filled with 3.27 g of immobilized enzyme.

REFERENCE EXAMPLE 1

Effect of Drying Technique on Fat Extraction

Figure 1:
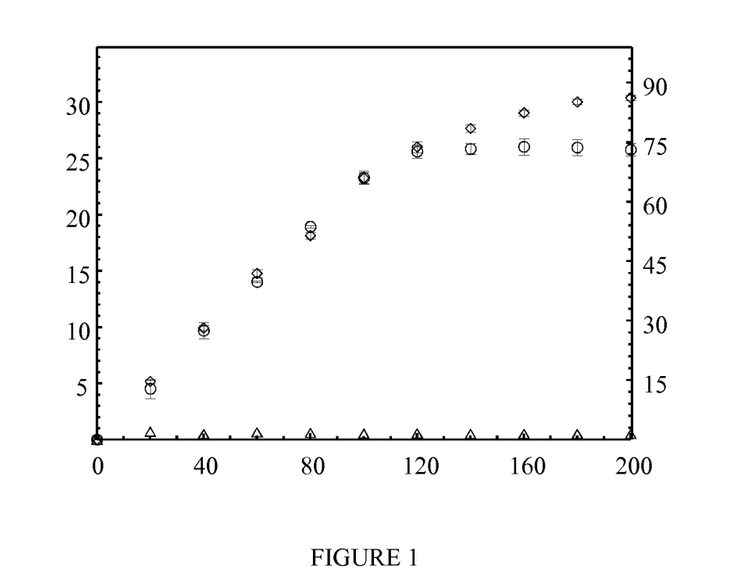
FIG. 1 illustrates the fat extracted yield per dried sample of Australian lamb leg meat samples (y-axis, left scale) and extraction efficiency (y-axis, right scale) as a function of the net volume of $SC\text{-}CO_2$ passed in ml (x-axis), under extraction conditions of 45° C., 300 bar and 3 ml min$^{-1}$ flow rate, where the meat was initially either vacuum-dried (marked by diamonds) or freeze-dried (marked by circles) compared to that when the meat was not dried (marked by triangles).

In order to study the effect of sample water content on $SC-CO_2$ extraction yield, Australian leg sample was dried using vacuum and freeze-drying and subjected to the SFE system at 45° C., 300 bar and 3 ml min$^{-1}$. Results from these two drying techniques were compared with that of fresh sample, as shown in FIG. 1. The presented data are averages of duplicate runs and the reproducibility of experimental results was confirmed from the error bars, shown on the figure, which were less than 1%. At the beginning of extraction, there was a linear dependence between extracted fat and passed $CO_2$ and the rate of extraction was almost constant.

In this region of extraction, excess amount of fat is available in the sample and so the extraction rate depends on the fat solubility in $SC-CO_2$. This was followed by a transition region, when the fat amount was depleted and the extraction became diffusion-limited, resulting in a decrease in extraction rate. In this region, $SC-CO_2$ had to diffuse into the particles and dissolve the internal fat and diffuse back out of the particles. In the last region, there was no more extractable fat and the extraction curve approached a constant value.

After passing 200 ml of $CO_2$, the SFE system was able to extract 72.6 and 85.7% of total amount of fat present using freeze- and vacuum-dried samples, respectively. This corresponds to 30.4% yield for the vacuum dried sample and 25.76% for the freeze dried sample. However, when un-dried (control) sample was used, $SC-CO_2$ was only able to extract less than 2% of the total fat content. It is believed that the water present in the control sample forms a film around the fat particles and prevents $SC-CO_2$ from contacting and hence extracting the fat.

It was also noticed that extraction from vacuum-dried sample was more efficient, as a result of the somewhat better water removal from the meat matrix. However, the extraction yields, using both drying techniques, were identical in the first 120 ml of passed $CO_2$.

REFERENCE EXAMPLE 2

Effect of Lamb Meat Source and Cut

Figure 2:
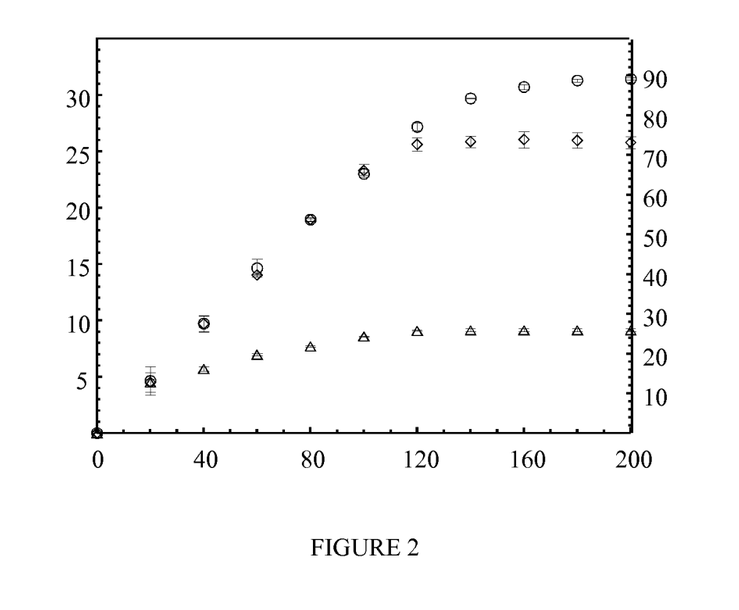
FIG. 2 illustrates the fat extracted yield per dried sample of lamb meat samples (y-axis, left scale) and extraction efficiency (y-axis, right scale) as a function of the net volume of $SC\text{-}CO_2$ passed in ml (x-axis), under extraction conditions of 45° C., 300 bar and 3 ml min$^{-1}$ flow rate, where the meat samples were either from an Australian shoulder cut (marked by circles), an Australian leg cut (marked by diamonds) or an Indian leg cut (marked by triangles).

The efficiency of supercritical fluid extraction (SFE) using samples from different sources and cuts were compared. FIG. 2 shows extraction yields and efficiency curves at 45° C., 300 bar and 3 ml min$^{-1}$ for three different freeze-dried samples. The results were in good agreement with solvent extraction results, which showed that Australian samples contain larger amounts of fat compared to the Indian leg. $SC-CO_2$ was able to extract 25.8, 31.4 and 9.1% fat from Australian leg, Australian shoulder and Indian leg, respectively. This corresponded to 72.7, 88.6 and 25.7% extraction efficiency, respectively.

It can be noted that for the first 20 ml of passed $SC-CO_2$, 4.5% fat from Indian leg meat was extracted, after that further increase of passed $SC-CO_2$ resulted in slight change until reaching a maximum yield of 9.1% after passing 200 ml of $SC-CO_2$. The high solubility in the first 20 ml is mainly because this region is the solubility-limited region and the fat has a high solubility in $SC-CO_2$. In spite of the fact that the freeze dryer removed 75% of the sample weight as water, the amount of water remaining in the dried sample may still have been high in comparison with sample fat content, resulting in relatively low system efficiency for extracting the fat. On the other hand, in the Australian samples, 23% of initial sample weight was extracted in the first 100 ml of passed $SC-CO_2$. The difference between Australian leg and shoulder yields was probably due to the amount of water that was present in the samples and the ability of $SC-CO_2$ to penetrate and extract the fat present inside the respective matrixes.

The results also confirmed the effectiveness of $SC-CO_2$ extraction compared to the soxhlet extraction. Around 75% of initial fat content was extracted in only 70 min whereas in soxhlet extraction 250 ml of n-hexane was consumed and took about 6 hours to extract all present fat. Moreover, soxhlet extraction required heating of the extracted sample to remove residual solvent.

REFERENCE EXAMPLE 3

Effect of Grinding

Breaking the sample down into small particles leads to exposure of soluble fats that are otherwise present in the solid matrix and renders them more easily accessible to the solvent. Increasing surface area and reducing diffusion path led to an increase in mass transfer of the dissolved fat.

Figure 3:
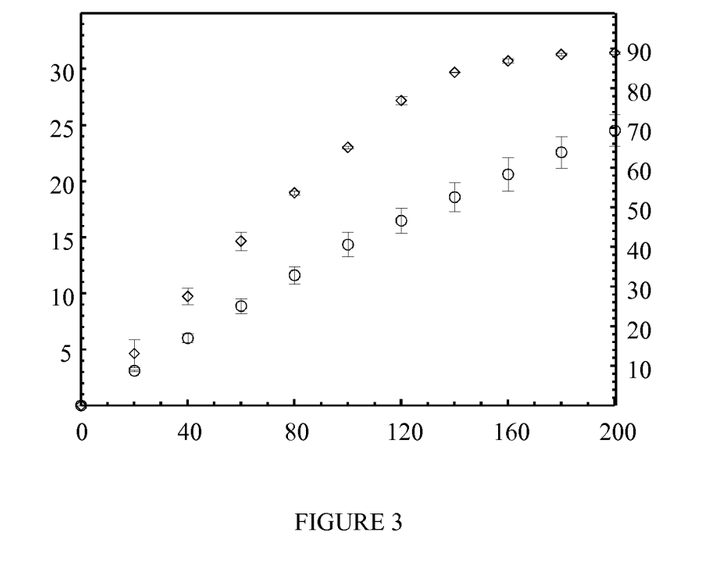
FIG. 3 illustrates the fat extracted yield per freeze dried sample of Australian lamb shoulder meat samples (y-axis, left scale) and extraction efficiency (y-axis, right scale) as a function of the net volume of $SC\text{-}CO_2$ passed in ml (x-axis), under extraction conditions of 45° C., 300 bar and 3 ml min$^{-1}$ flow rate, where the freeze dried meat was initially either ground (marked by diamonds) or unground (marked by circles).

Sample grinding was performed using a mechanical grinder (Molinex) and fat was extracted at 45° C., 300 bars and 3 ml min$^{-1}$. The effect of sample grinding on extraction yield and SFE efficiency is shown in FIG. 3. The results show that sample grinding improved extraction yield. Nevertheless, it should be noted that SC-$CO_2$ was also successful in extracting fat from un-ground meat, which is promising for using meat chunks in the future.

REFERENCE EXAMPLE 4

Effect of Operating Conditions

I) SC-$CO_2$ Flow Rate

Figure 4:
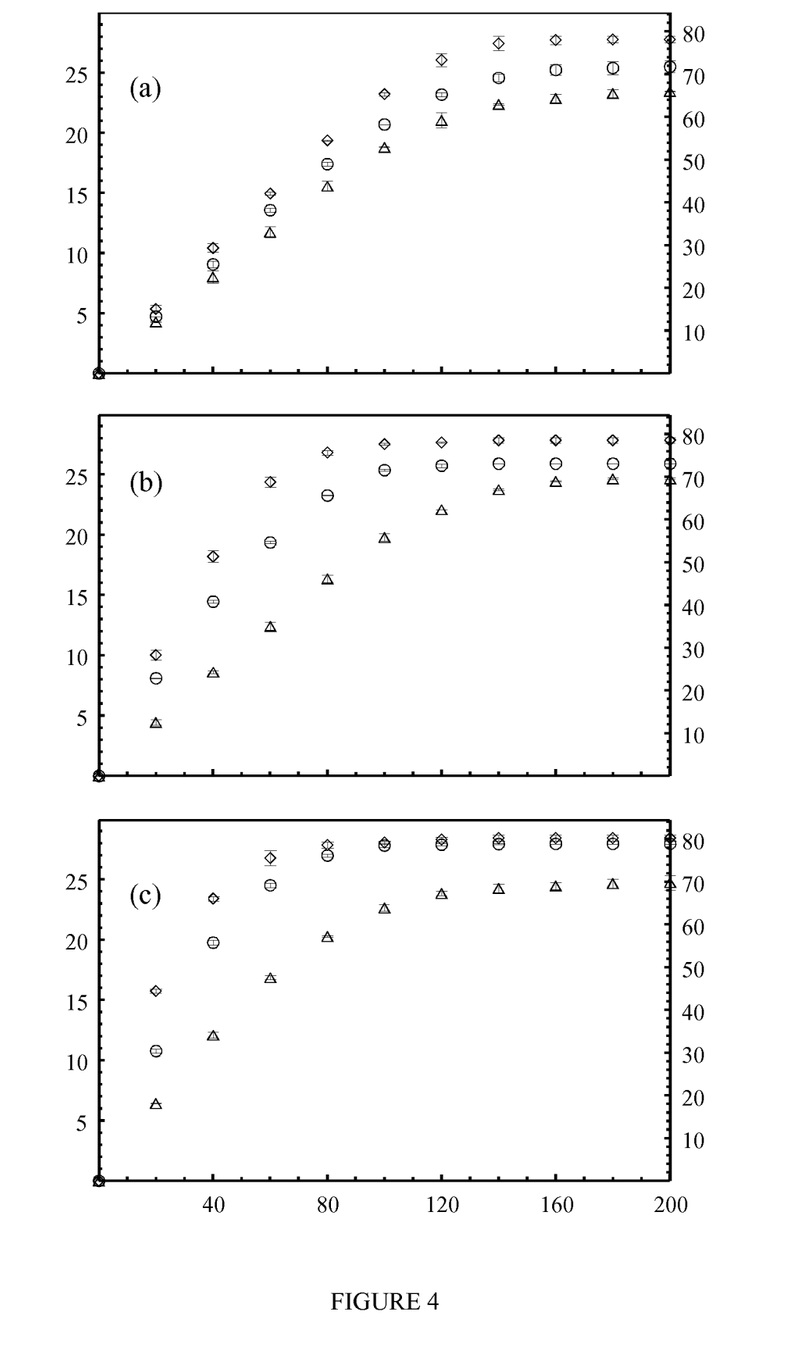
FIG. 4 illustrates the fat extracted yield per freeze dried sample of Australian lamb shoulder meat samples (y-axis, left scale) and extraction efficiency (y-axis, right scale) as a function of the net volume of $SC\text{-}CO_2$ passed in ml (x-axis), at a temperature of 35° C. at flow rates of 3 ml min$^{-1}$ (marked by diamonds), 4 ml min$^{-1}$ (marked by circles) and 5 ml min$^{-1}$ (marked by triangles), at atmospheric pressures of (a) 300 bar, (b) 400 bar and (c) 500 bar.

The effect of SC-$CO_2$ flow rate on extraction yield and efficiency from ground, freeze-dried Australian shoulder meat samples using different pressures and SC-$CO_2$ flow rates at a temperature of 35° C. and pressures of 300 bar, 400 bar and 500 bar is shown in FIG. 4($a$-$c$). As shown, extraction yield decreased as SC-$CO_2$ flow rate increased. This is likely to be due to the decrease of residence time, resulting in shorter contact time between the solvent and the fat. Therefore, the SC-$CO_2$ leaving the extraction cell may not be saturated with fat. This indicated that the intra-particle diffusion resistance may control the extraction. It can also be noted that as the pressure increased, the difference between 3 and 4 ml min$^{-1}$ flow rates tended to reduce. This is probably because increasing the pressure increases the solubility, and hence both 3 and 4 ml min$^{-1}$ have sufficient time to reach saturation.

II) Extraction Pressure

Figure 5:
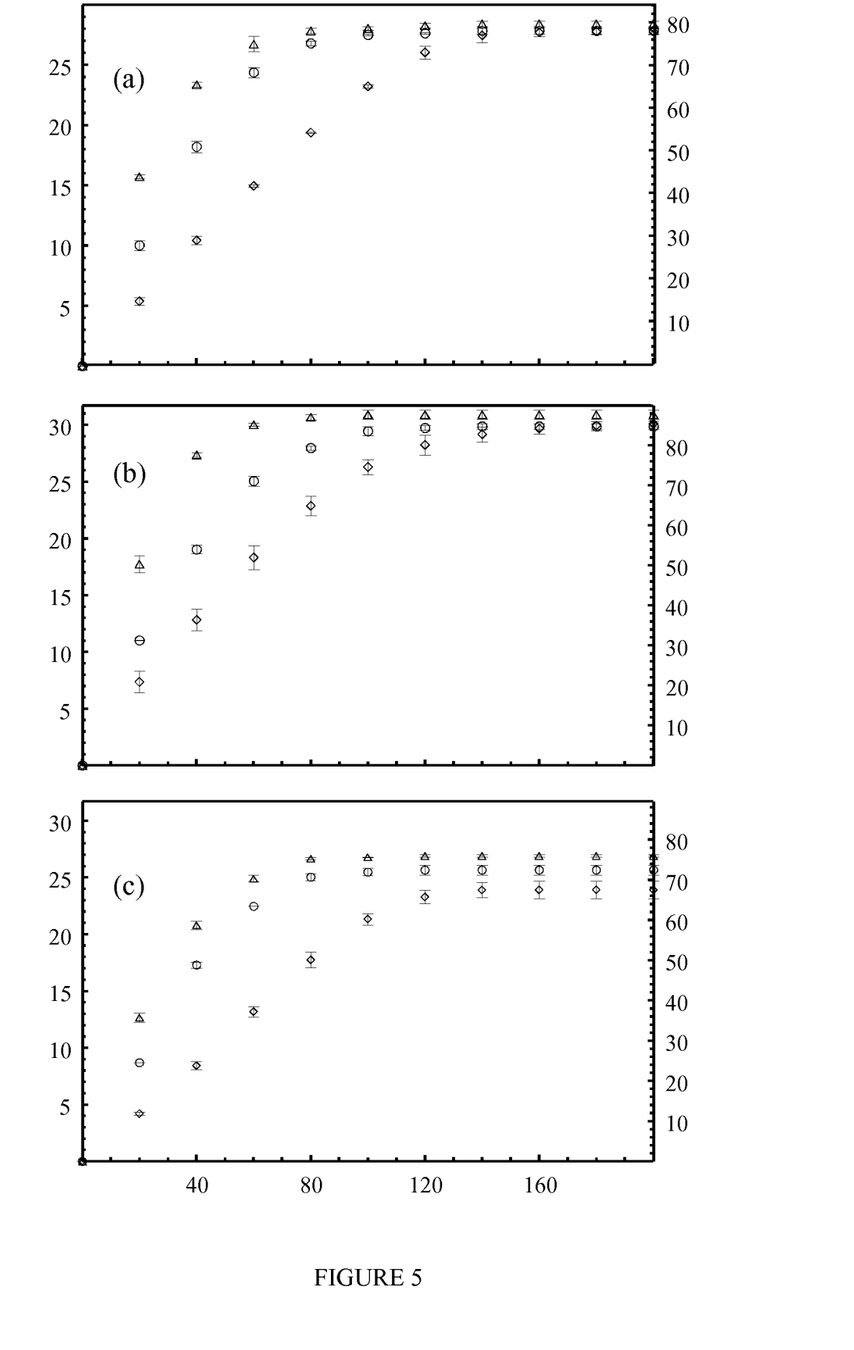
FIG. 5 illustrates the fat extracted yield per freeze dried sample of Australian lamb shoulder meat samples (y-axis, left scale) and extraction efficiency (y-axis, right scale) as a function of the net volume of $SC\text{-}CO_2$ passed in ml (x-axis), at a flow rate of 3 ml min$^{-1}$ and 300 bars (marked by diamonds), 400 bars (marked by circles) and 500 bars (marked by triangles), at temperatures of (a) 35° C., (b) 45° C. and (c) 55° C.

The effect of pressure on extraction yield and efficiency at flow rate of 3 ml min$^{-1}$ and temperatures of 35, 45 and 55° C. is shown in FIG. 5($a$-$c$). For the three operating temperatures, yield and efficiency increased with increasing pressure. This is probably due to the fact that as pressure increased, the SC-$CO_2$ density increased and, therefore, solvation power of fat increased. For all temperatures studied, at 80 ml of passed $CO_2$ there was a significant increase in extraction yield with the pressure. This effect significantly decreased with the additional increase in the passed $CO_2$ leading to insignificant increase at 200 ml of passed $CO_2$.

III) Extraction Temperature

Figure 6:
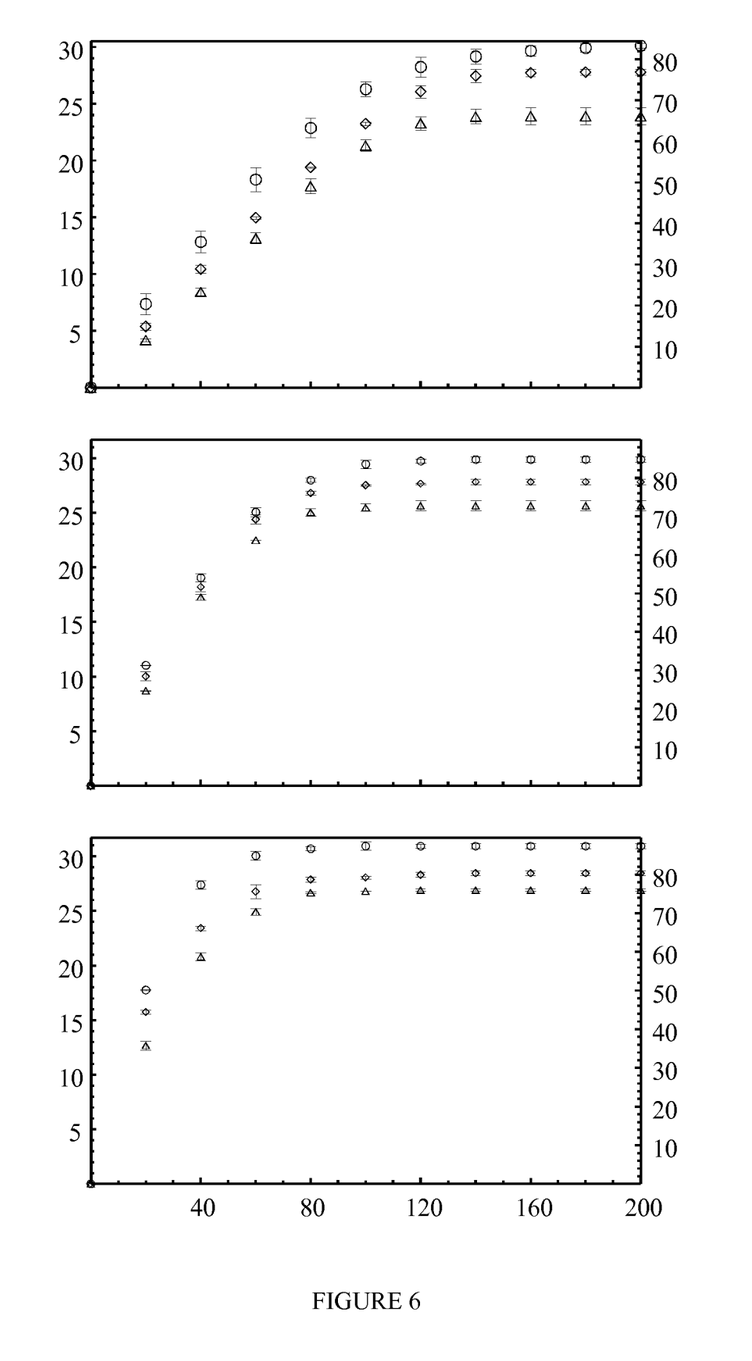
FIG. 6 illustrates the fat extracted yield per freeze dried sample of Australian lamb shoulder meat samples (y-axis, left scale) and extraction efficiency (y-axis, right scale) as a function of the net volume of $SC\text{-}CO_2$ passed in ml (x-axis), at a flow rate of 3 ml min$^{-1}$ and at 35° C. (marked by diamonds), 45° C. (marked by circles) and 55° C. (marked by triangles), at atmospheric pressures of (a) 300 bar, (b) 400 bar and (c) 500 bar.
Figure 7:
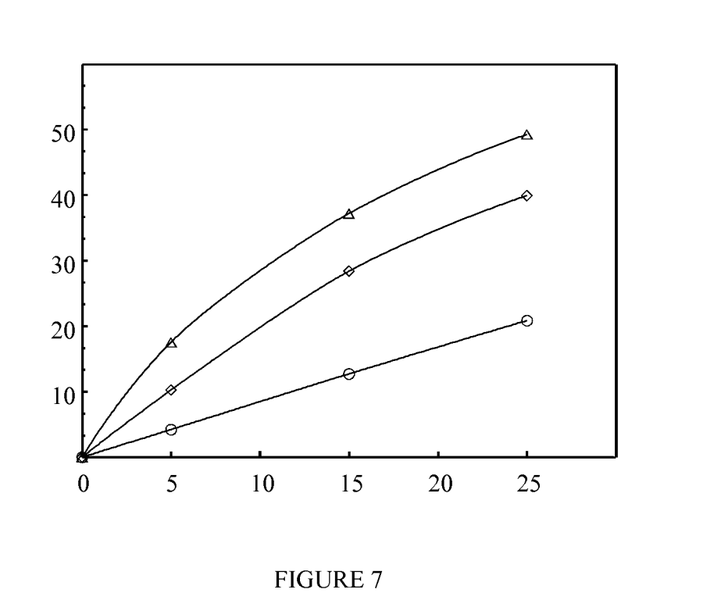
FIG. 7 illustrates the biodiesel FAME yield (y-axis) as a function of time in hours (x-axis) at a temperature of 50° C., 200 bars, 4:1 methanol molar ratio and different enzyme loadings, as percentage of initial fat, the enzyme loadings being 10% (marked by circles), 30% (marked by diamond) and 50% (marked by triangle), respectively.

FIG. 6($a$-$c$) shows effect of temperature on extraction yield and efficiency at flow rate of 3 ml min$^{-1}$ and at 300 bar, 400 bar and 500 bar. It can be noted that increasing extraction temperature from 35 to 45° C. increased extraction yield and the extraction rate, whereas a further increase to 55° C. decreased both the yield and initial extraction rate. This is probably due to the competing effect of $CO_2$ solvation (density) and fat volatility with the temperature. At constant pressure, $CO_2$ density decreases with increasing temperature, but at the same time the volatility of the fat increases. Since increasing temperature from 35 to 45° C. increased extraction yield and extraction rate, volatility effect was the dominant, whereas for further increase in temperature, density effect became dominant. Similar results were observed with other flow rates.

EXAMPLE 1

Effect of Enzyme Loading

In order to study the effect of enzyme quantity on biodiesel yield, Novozym 435 loading was varied from 10% to 50%, with a 20% interval (as a ratio to initial amount of fat extracted from lamb meat). Besides the amount of enzyme loading, all other variables were kept constant. Experiments were performed with 0.5 g fat, 4:1 methanol molar ratio at 50° C. and 200 bar. The FAME production yields are shown in FIG. 5.

It can be seen that FAME yield increased with increasing enzyme loading. At 5 hours, the increase in FAME yield with enzyme loading was linear, but the effect started to deviate from linear behaviour at higher times, this deviation increasing as time increased. This is probably due to the approaching of the equilibrium yield as time increased, and hence the effect of enzyme loading tending to diminish.

Although the rate of reaction increased with increasing the enzyme loading, from an economical point of view and due to the high cost of the enzyme, the loading cannot be increased indefinitely. The results show that the yield increased significantly as the enzyme loading increased from 10% to 30%. However, this effect of enzyme loading became less significant as it increased from 30% to 50%. Therefore, the Example shows that it is not necessary to use enzyme loading higher than 30%.

EXAMPLE 2

Effect of Reaction Temperature

Figure 8:
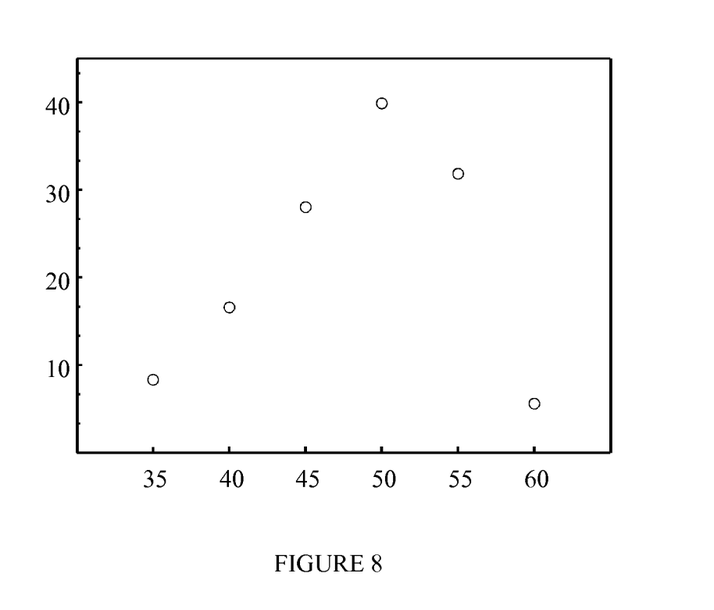
FIG. 8 illustrates the biodiesel FAME yield (y-axis) at 25 hours as a function of temperature in ° C. (x-axis) at 200 bars, 4:1 methanol molar ratio and 30% enzyme loading, as percentage of initial fat.

The effect of reaction temperature on FAME yield was determined by carrying out enzymatic reaction in SC-$CO_2$ medium at different temperatures in the range of 35° C. to 60° C. at 200 bars, 4:1 alcohol to fat molar ratio, 30% enzyme loading and 25 hr reaction time. As shown in FIG. 8, increasing the temperature from 35° C. to 50° C. resulted in increasing the yield from 8.3% to 39.8%. At reaction temperatures above 50° C., FAME dropped to 5.57% at 60° C.

The initial increase in the yield with temperature is likely to be mainly due to an increase in rate constants with temperature, and partly due to the reduction in mass transfer limitations. The sharp decrease in yield at temperatures above 50° C. is almost certainly due to the denaturation of the enzyme at higher temperatures. In addition to the deactivation of the enzyme, the presence of the inactive enzyme at the interface blocks the active enzyme from penetrating the interface, which further decreases the reaction rate.

EXAMPLE 3

Effect of Methanol to Fat Ratio

Figure 9:
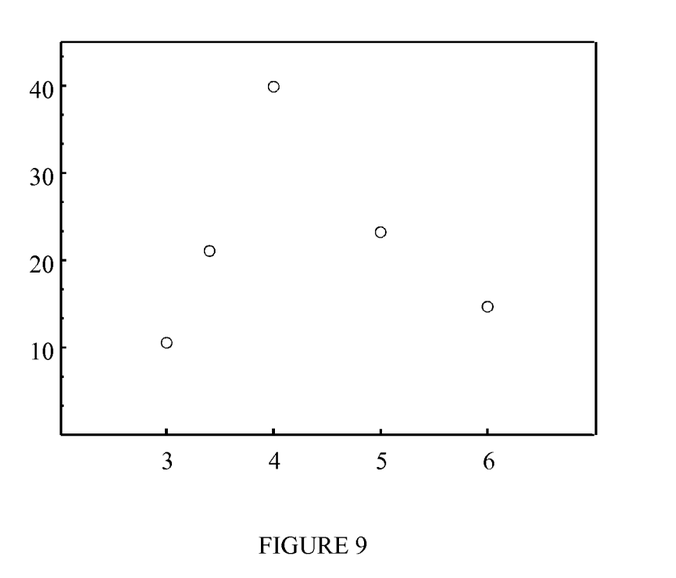
FIG. 9 illustrates the biodiesel FAME yield (y-axis) at 25 hours as a function of methanol molar ratio (x-axis) at 200 bars, 50° C. and 30% enzyme loading, as percentage of initial fat.

The molar ratio of methanol to fat is one of the most important variables affecting the yields of FAME. Stoichiometrically, to produce FAME three molecules of methanol are required to react with one molecule of extracted fat. Increasing molar ratio should increase forward reaction to produces more FAME. The effect of the molar ratio of methanol to fat was studied in the range between 3 and 6 on the yield of FAME formed. The results shown in FIG. 9 were obtained using different methanol to oil ratios, 30% enzyme loading at 50° C., 200 bar and for 25 hr reaction time. As expected, increasing methanol to fat ratio from stoichiometric resulted in increased FAME yield to an optimum value then the yield dropped. Highest FAME yield was obtained at 4:1 methanol to oil ratio. An increase of the molar ratio from 3:1 to 4:1 increased FAME yield more than three time yielding 39.9%. The drop after 4:1 ratio can probably be attributed to inhibition of lipase by the contact with insoluble methanol, tending to strip the active water from the active sites of the enzyme due to its strong polarity.

EXAMPLE 4

Continuous Integrated Extraction-Reaction System

Figure 11:
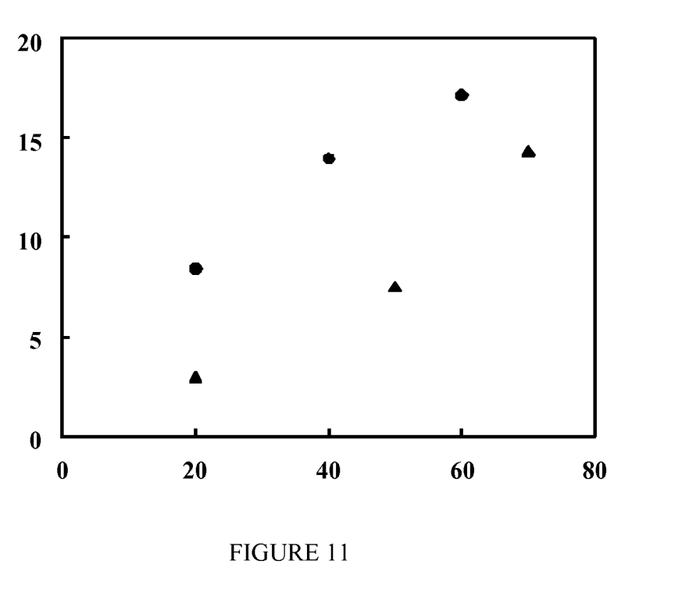
FIG. 11 illustrates continuous biodiesel production (y-axis) as a function of time in minutes (x-axis) at 200 bars, 45° C. extraction temperature and 50° C. reaction temperature, using 2.6 g freeze dried meat and 3.27 g enzyme, for both a second reaction cycle (marked by circles) and a third reaction cycle (marked by triangles).

About 2.5 g freeze-dried samples were charged into the extraction cell. The reaction cell, of 10 ml total volume, was completely packed with 3.27 g immobilized lipase. The operating conditions chosen were 0.5 ml min$^{-1}$, 200 bars and temperatures of 45° C. and 50° C. for the extraction and reaction cells, respectively. After 40 min of operation, the amount of biodiesel produced was 17.7 mg. The meat sample was then replaced with a new 2.5 g of freeze-dried samples, while keeping the enzyme unchanged, and after 40 min, 14.0 mg of biodiesel was produced. The meat sample was replaced again, while keeping the enzyme unchanged, and after 60 min 14.4 mg of biodiesel was produced. The biodiesel production as a function of time is shown in FIG. 11 for the second and third cycles.

The invention claimed is:

1. A process for the production of biodiesel, the process comprising:
   providing edible animal flesh including animal meat and animal fat;
   flowing a supercritical carbon dioxide carrier through the animal flesh thereby to extract animal fat from the animal flesh so as to obtain:
      an edible product comprising edible animal flesh having a reduced fat content; and
      a feedstock for biodiesel production comprising animal fat in the supercritical carbon dioxide carrier;
   separating the edible product and the feedstock from one another; and
   reacting the feedstock comprising said animal fat in said supercritical carbon dioxide carrier with one or more biodiesel producing reactants, thereby producing biodiesel.

2. The process according to claim 1, wherein the step of reacting the feedstock comprises reacting said animal fat in said supercritical carbon dioxide carrier with a $C_{1-5}$ alcohol or $C_{1-5}$ ester thereof in the presence of a lipase catalyst.

3. The process according to claim 2, wherein said $C_{1-5}$ alcohol or $C_{1-5}$ ester thereof is selected from the group consisting of methanol, ethanol, methyl methanoate, methyl ethanoate, ethyl methanoate and ethyl ethanoate.

4. The process according to claim 2, wherein said $C_{1-5}$ alcohol or $C_{1-5}$ ester thereof is methanol.

5. The process according to claim 2, wherein the molar ratio of $C_{1-5}$ alcohol or $C_{1-5}$ ester thereof to triglycerides in said fat is from 3:1 to 5:1.

6. The process according to claim 2, wherein the step of reacting said fat is carried out at a reaction temperature of from 40 to 50° C.

7. The process according to claim 2, wherein said lipase enzyme is immobilized.

8. The process according to claim 1, wherein the step of providing edible animal flesh comprises one of
   providing edible animal flesh having a low concentration of water in the animal flesh; and reducing a concentration of water in the animal flesh.

9. The process according to claim 8, wherein the step of reducing the concentration of water in the animal flesh comprises freeze-drying or vacuum-drying the animal flesh.

10. The process according to claim 8, wherein the animal flesh that has a low concentration of water has a concentration of water of 15 wt% or less.

11. The process according to claim 1, which comprises grinding the animal flesh before the step of flowing supercritical carbon dioxide.

12. The process according to claim 1, which after the step of flowing supercritical carbon dioxide, further comprises formulating the edible animal flesh having a reduced fat content into a food product.

13. The process according to claim 1, which process is carried out in an integrated reactor system comprising:
   a fat extraction unit comprising a first reactor for carrying out the step of flowing supercritical carbon dioxide, which unit comprises
      means for supplying the animal flesh to said first reactor,
      means for adjusting the temperature of said first reactor,
      means for supplying supercritical carbon dioxide to said first reactor, and
      means for removing from said first reactor fat in a supercritical carbon dioxide carrier; and
   a biodiesel production unit comprising a second reactor for carrying out the step of reacting said fat, which unit comprises
      means for adjusting the temperature of said second reactor,
      means for supplying to said second reactor fat in a supercritical carbon dioxide carrier that has been removed from said fat extraction unit,
      means for supplying a $C_{1-5}$ alcohol or $C_{1-5}$ ester thereof to said second reactor, and
      means for removing biodiesel from said second reactor.

14. The process according to claim 13, wherein said integrated reactor system is adapted so that said first reactor and said second reactor operate at substantially the same temperature and pressure.

15. An integrated reactor system as claimed in claim 13.

16. Biodiesel obtainable by carrying out the process as claimed in claim 1.

17. The process according to claim 1, wherein the edible animal flesh includes at least one of lamb meat and lamb fat.

18. An edible product obtained by carrying out the process as claimed in claim 1.

19. The process according to claim 1, wherein the process is for contemporaneous production of the edible animal flesh and the biodiesel.

20. The process according to claim 1, wherein the step of flowing the supercritical carbon dioxide carrier through the animal flesh, provides for dissolution of the animal fat in the supercritical carbon dioxide carrier, thereby to provide for said reduction of the fat content of the animal flesh.

21. The process according to claim 1, wherein the step of flowing the supercritical carbon dioxide carrier through the animal flesh provides supercritical carbon dioxide carrier having the fat dissolved therein.

* * * * *